United States Patent [19]

Lewbart

[11] Patent Number: 4,511,511

[45] Date of Patent: Apr. 16, 1985

[54] PREDNISOLONE DERIVATIVES

[75] Inventor: Marvin L. Lewbart, Media, Pa.

[73] Assignee: Crozer-Chester Medical Center, Chester, Pa.

[21] Appl. No.: 450,155

[22] Filed: Dec. 15, 1982

[51] Int. Cl.$^3$ .............................................. C07J 5/00
[52] U.S. Cl. ...................... 260/239.55 D; 260/397.1; 260/397.45
[58] Field of Search ....... 260/397.1, 397.45, 239.55 D

[56] References Cited

U.S. PATENT DOCUMENTS 3,944,577  3/1976  Laurent et al. .................. 260/397.1

OTHER PUBLICATIONS

Solimon, M. R. I. et al. "6th Ann. Clin. Symp. Proc. Res. Cline. Application Corticoids", Proceedings (Dec. 1981), a paper titled New Antiinflammatory Steroids: Steroid-21-oate Esters.

Heiman et al., "Steroids", vol. 38, No. 4, (1981), p. 2799.

Lee et al., (2), "Science", Feb. 1982, vol. 215, pp. 989–991.

Lee et al., "Research Communications in Chemical Pathology and Pharmacology", vol. 27, No. 3, (1980), p. 611.

Soliman et al., "Research Communications in Chemical Pathology and Pharmacology", vol. 33, No. 2, Aug. 1981.

Primary Examiner—Elbert L. Roberts
Attorney, Agent, or Firm—Sughrue, Mion, Zinn, Macpeak & Seas

[57] ABSTRACT

Novel prednisolone derivatives modified at C-17, C-20 and/or C-21 positions. Many of the compounds are anti-inflammatory agents which do not significantly suppress the pituitary-adrenal axis.

12 Claims, No Drawings

PREDNISOLONE DERIVATIVES

BACKGROUND OF THE INVENTION

The present invention relates to compounds which broadly may be considered as pregnadienoic acid derivatives. In addition, the compounds with which the present invention is concerned are derived from a basic prednisolone ring structure and thus may be termed prednisolone derivatives. Hereinafter the terms "pregnadienoic acid derivatives" and "prednisolone derivatives" will be used interchangeably to designate the general class of compounds with which the compounds of the present invention are believed to be associated.

Prednisolone is a potent pharmaceutical agent which has been commercially available for many years. Prednisolone is characterized by pronounced anti-inflammatory activity, when administered locally or systemically, coupled with a significant suppression of the pituitary-adrenal axis. Usually, prednisolone is administered for its anti-inflammatory effect and the associated pituitary-adrenal axis inhibition is often considered as a serious, major side effect resulting from the administration of prednisolone. Indeed, adrenal inhibition is often considered the major disadvantage of using many of the corticosteroid anti-inflammatory drugs. Even so, one should bear in mind that in certain disease states and medical conditions, such as manifestations of hyperadrenocorticalism, suppression of plasma cortisol is desired, so in that instance the drug's anti-inflammatory activity could be considered an undesirable side effect.

Most often, the corticosteroid compounds are being administered for their anti-inflammatory effect. Although a number of potent corticosteroid compounds have been commercially developed for use as local and systemic anti-inflammatory agents, essentially all of them produce an undesired adrenal inhibition side effect, even when only administered topically, such as where large surface body areas are involved and/or prolonged treatment times are needed.

One approach to the problem of pituitary adrenal axis suppression occurring from topical administration of steroid drugs has been to employ dosage forms tailored for local application while reducing systemic absorption. Recently, another approach has been investigated, which involves the chemical modification of corticosteroid compounds to develop chemical structures which divorce the anti-inflammatory activity of the corticosteroid from the pituitary-adrenal suppression activity thereof. Some successes have been reported in this area, which is the general area of structural-activity relationships to which the present invention is directed. Although the main thrust has been to structurally modify base corticosteroid structures to retain or enhance anti-inflammatory properties while reducing pituitary adrenal axis suppression, the inventor again notes that at times the medical condition being treated requires the opposite approach, that is to retain the pituitary adrenal axis suppression properties while reducing the anti-inflammatory characteristics of the steroid drug.

As will be explained more fully hereinbelow, the present invention is concerned with corticosteroid compounds, which as noted above may broadly be considered as pregnadienoic acid derivatives or as prednisolone derivatives, which compounds are characterized by a pharmacological spectrum of activity which is (A) significant anti-inflammatory activity without significant pituitary-adrenal axis suppression, (B) significant adrenal inhibition without significant anti-inflammatory activity or (C) both of significant anti-inflammatory activity and significant pituitary-adrenal axis suppression activity.

Henry J. Lee and co-workers at Florida A & M University, Tallahassee, Fla., have published a number of papers on their so-called "P4" and "P8" compounds. "P8" is stated to be methyl prednisolonate; "P4". is described as methyl 20-dihydroprednisolonate. In order to avoid any ambiguity in nomenclature, "prednisolone" is used herein to designate the structure 11β,17,21-trihydroxy-1,4-pregnadiene-3,20-dione.

Thus, methyl prednisolonate is the same as the compound named methyl 11β,17-dihydroxy-3,20-dioxo-1,4-pregnadien-21-oate. Structurally, "P4" and "P8" are illustrated by Lee et al as follows:

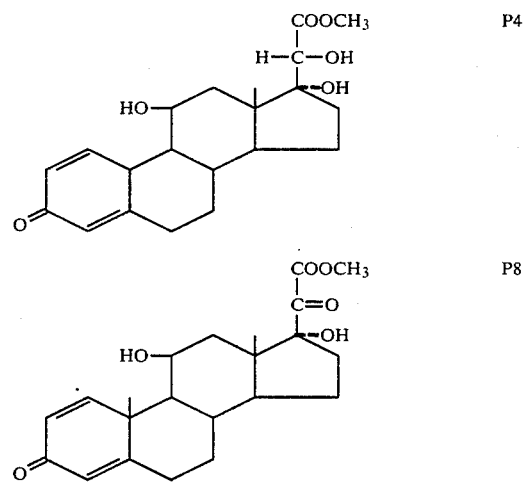

Regarding the work of Lee et al, see Solimon, M. R. I., et al "New Anti-inflammatory Steroids: Steroid-21-oate Esters" *6th Ann. Clin. Sympo., Prog. Res. Clin. App. Corticoids, Proceedings of December* 1981; Lee, Henry J. et al, "Binding of Glucocorticoid 21-oic Acids and Esters to Molybdate-Stabilized Hepatic Receptors", *Journal of Steroid Biochemistry*, Vol. 14, p. 1325 (1981); Heiman, Ann S., et al, "Stabilization of Rat Liver Lysozymes by New Anti-Inflammatory Steroids In Vitro," *STEROIDS*, Vol. 38, No. 4, p. 2799 (1981); Lee, Henry J., et al, "Anti-Inflammatory Steroids Without Pituitary-Adrenal Suppression," *Science*, Vol. 215, p. 989 (1982); Lee, Henry J., et al, "Anti-Inflammatory Activity of Two Novel Derivatives of Prednisolone", *Research Communications in Chemical Pathology and Pharmacology*, Vol. 27, No. 3, p. 611 (1980); Soliman, M. R. I., et al, "Local Anti-Inflammatory Activity of Acid Ester Derivatives of Prednisolone," *Research Communications in Chemical Pathology and Pharmacology*, Vol. 33, No. 2, (1981); DePetrillo, Thomas et al, "Two Anti-Inflammatory Steroids Which Neither Inhibit Skin Collagen Synthesis Nor Cause Skin Atrophy," (in preparation).

Lee et al synthesized their "P4" and "P8" materials using procedures worked out and published by the present inventor many years prior to the Lee et al work. See, Lewbart, M. L., et al, "Preparation and Properties of Steroidal 17,20- and 20,21-Acetonides Epimeric at C-20. II Derivatives of Cortisol and Cortisone", *J. Org. Chem.*, 34, p. 3513 (1969). Other Lewbart et al references noted by the Lee et al publications, regarding synthesis procedures, are "Conversion of Steroid-17-yl Glyoxals to Epimeric Glycolic Ester," *J. Org. Chem.,* 28, p. 1779 (1963) and "Oxidation of Steroidal Alpha-Ketols to Glyoxals with Cupric Acetate," *J. Org. Chem.,* 28, p. 2001, (1963). In addition, the present inventor has co-authored a number of other articles published in the *Journal of Organic Chemistry* related to steroidal synthesis steps; however, the present invention is not concerned with steroidal compound preparation.

In reviewing the Lee et al published articles it is found that the "P4" material as synthesized and tested in accordance with the Lee et al publications would in actuality be a mixture of compounds and would be expected to contain both the 20-α and 20-β epimers of methyl 20-dihydroprednisolonate. This may explain the different results obtained at times by Lee et al. Subsequent contacts between the present inventor and Lee have confirmed that Lee et al's published "P4" comprises an epimeric mixture, usually with the 20-α and 20-β epimers being present in a ratio of about 10:1, with the "P4" material also containing small amounts of unknown impurities.

Laurent et al, U.S. Pat. No. 3,994,577, disclose pregnan-21-oic acids and esters thereof stated to have topical anti-inflammatory activity with substantially no systemic activity. The Laurent et al compounds are characterized by carbonyl at C-20. In addition, Laurent et al disclose synthesis of their target compounds through intermediates of their formula III, as follows:

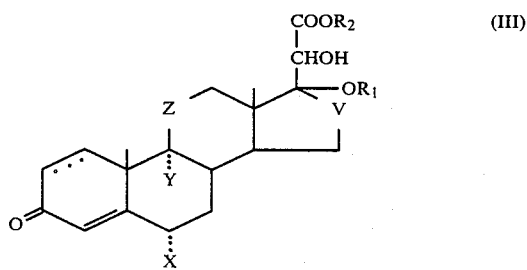

which includes the methyl ester of 11β,17α,20ε-trihydroxy-3-oxo-1,4-pregnadien-21-oic acid (Example 15 of U.S. Pat. No. 3,944,577). Thus, Laurent et al, also using the copper acetate method of Lewhart et al, do correctly note the epimeric mixture (20ε). Related work of Laurent et al is found in "New Biologically Active Pregnan-21-oic Acid Esters", *J. of Steroid Biochemistry,* 6, p. 185 (1975), where many C-20 epimers, but not including those of the present invention, are described. Laurent et al are concerned with synthesis of corticoid derivatives for use as possible local anti-inflammatory agents without systemic side effects. Their preferred compounds include a fluorine ring substituent. Another disclosure of the methyl ester of 20-dihydro-prednisolonate is found in German 1173467 by Daase et al.

SUMMARY OF THE INVENTION

It is an object of the present invention to provide novel pregnadienoic acid derivatives useful as anti-inflammatory agents.

Another object of this invention is to provide novel anti-inflammatory pregnadienoic acid derivatives characterized by reduced adrenal inhibition properties.

A further object of the present invention is to provide novel pregnadienoic acid derivatives which inhibit the pituitary-adrenal axis without exerting a pronounced anti-inflammatory effect.

Still another object of this invention is to provide novel pregnadienoic acid derivatives capable of exerting both a pronounced anti-inflammatory effect and a pronounced adrenal inhibition effect.

Another object of the present invention is to provide novel pharmaceutical compositions including as an active compound at least one novel pregnadienoic acid derivative capable of exerting one or both of an anti-inflammatory effect and an adrenal inhibition effect.

Other objects of the present invention involve the administration of at least one of the novel pregnadienoic acid derivatives disclosed herein, locally or systemically, to a patient suffering from an inflammatory disease or condition of the type herebefore treated by steroid therapy, in an amount effective to relieve inflammation without significant inhibition of adrenal function. Similarly, a novel pregnadienoic acid derivative of the present invention can be administered to a patient requiring pituitary adrenal axis suppression, without providing significant anti-inflammatory activity.

Other objects of this invention will be apparent to the skilled artist from the Detailed Description of the Invention hereinafter.

In accordance with the present invention, there are provided novel pregnadienoic acid derivatives of the formula (I)

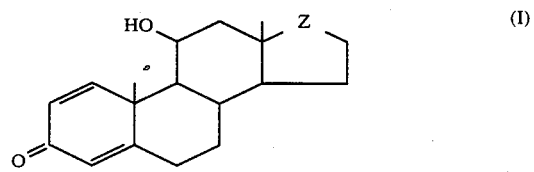

wherein Z is a group represented by the formula (II)

wherein $R_1$ is selected from the group consisting of hydrogen, substituted or unsubstituted alkyl, substituted or unsubstituted alkenyl, substituted or unsubstituted alkynyl, substituted or unsubstituted aryl, substituted or unsubstituted arylalkyl, and substituted or unsubstituted heterocyclic groups, and each of R and $R_2$ is independently selected from the group consisting of hydrogen, substituted or unsubstituted alkyl, substituted or unsubstituted alkenyl, substituted or unsubstituted alkynyl, substituted or unsubstituted aryl, substituted or unsubstituted arylalkyl, substituted or unsubstituted acyl and substituted or unsubstituted heterocyclic groups, and wherein $R_1$ and R or R and $R_2$ can combine to form a substituted or unsubstituted heterocyclic ring containing from 5 to 8 ring atoms, which ring may include one or two additional hetero atoms selected from the group consisting of oxygen, nitrogen and sulfur atoms, with the provisos (1) that when $R_1$ is methyl and R and $R_2$ are both hydrogen that the included compounds are only the 20-α and 20-β epimers and (2) that only one of $R_1$, R and $R_2$ can be an aryl, arylalkyl or heterocyclic group at the same time and (3) at least one of $R_1$, R and $R_2$ is not hydrogen.

Preferably, Z is selected from the group consisting of:

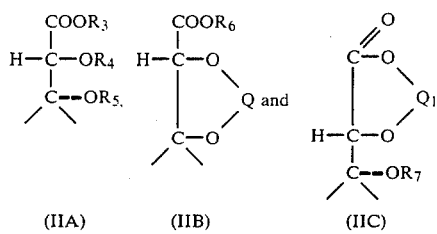

wherein each of $R_3$ and $R_6$ is selected from the group consisting of hydrogen and lower alkyl, and each of $R_4$, $R_5$ and $R_7$ is selected from the group consisting of hydrogen, lower alkyl and lower acyl, with at least one of $R_3$, $R_4$ and $R_5$ being other than hydrogen; each of Q and $Q_1$ is selected from the group consisting of

wherein X is O or S,

and $-(CH_2)_n-$ wherein each of $R_8$ and $R_9$ is independently selected from the group consisting of hydrogen, lower alkyl, aryl, arylalkyl, alkanoyl or aroyl, and n is an integer selected from 2 to 10.

Preferred compounds are characterized by one or more of the following features:
(1) $R_3$ is lower alkyl
(2) $R_5$ or $R_7$ is hydrogen
(3) Q is

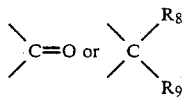

wherein $R_8$ and $R_9$ are lower alkyl
(4) $Q_1$ is

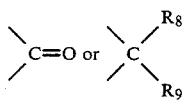

wherein $R_8$ and $R_9$ are lower alkyl

DETAILED DESCRIPTION OF THE INVENTION

As disclosed hereinbefore, the present invention is directed to novel steroid compounds of the type principally characterized by local anti-inflammatory activity and/or systemic anti-inflammatory activity and/or systemic adrenal cortex inhibition activity. More specifically, the compounds of the present invention may broadly be considered from a chemical structural standpoint as prednisolone derivatives or analogs thereof, and/or pregnadienoic acid derivatives or analogs thereof.

Certain of the compounds of the present invention are unusual in that they exhibit a significant anti-inflammatory activity with comparatively reduced adrenal suppression. Other compounds of the invention are unusual in that they cause a significant adrenal inhibition coupled with comparatively reduced anti-inflammatory activity. Therefore, compounds of the first type should be useful in the treatment of inflammatory diseases heretofore treated by topical, local, and/or systemic administration of steroids, for example, rheumatoid arthritis, asthma, localized allergic inflammation, a variety of localized rheumatologic disorders requiring intra-articular or soft tissue administration, neoplastic disease, hematogic disorders, etc., while compounds of the second type should prove useful in the treatment of Cushing's Disease, adrenocortical carcinoma and adrenogenital syndrome. Of course, some of the compounds of this invention ar similar in pharmacological spectrum to conventional steroids in that they exhibit a significant anti-inflammatory effect along with significant adrenal suppression.

The compounds of the present invention may be represented by the following generic formula (I)

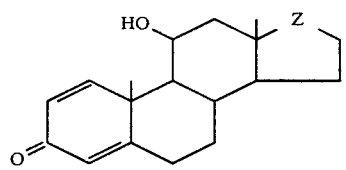

wherein Z is

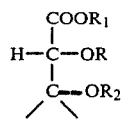

In formula (II), $R_1$, R and $R_2$ can independently be selected from many different types of groups as described in greater detail hereinbelow; however, at least one of $R_1$, R and $R_2$ must be a group other than hydrogen. In addition, when $R_1$ is methyl and both R and $R_2$ are hydrogen, the compound cannot be an epimeric mixture, that is, the compound must be either the 20α epimer or the 20β epimer. With these initial caveats in mind, $R_1$, R and $R_2$ may be defined as follows:

$R_1$ is hydrogen, substituted or unsubstituted alkyl, substituted or unsubstituted alkenyl, substituted or unsubstituted alkynyl, substituted or unsubstituted aryl, substituted or unsubstituted arylalkyl and substituted or unsubstituted heterocyclic groups.

By "substituted or unsubstituted alkyl" is meant straight or branched chain alkyl containing from 1 to 10 carbon atoms. Preferably, the alkyl group is lower straight chain alkyl (up to about 4 carbon atoms) and is unsubstituted. Where a substituent would be present, it could be selected from hydroxy, halogen, nitro, mercapto and the like.

By "substituted or unsubstituted alkenyl" is meant straight or branched chain alkenyl (having a double bond) containing 2 to 10 carbon atoms. Preferably, the alkenyl group would be lower straight chain alkenyl (up to about 4 carbon atoms) and is unsubstituted. Where a substituent would be present, it could be selected from hydroxy, halogen, nitro, mercapto and the like.

By "substituted or unsubstituted alkynyl" is meant straight or branched chain alkynyl (having a triple bond) containing 3 to 10 carbon atoms. Preferably, the alkynyl group is lower straight chain alkynyl containing up to about 5 carbon atoms. Where a substituent would be present, it could be selected from hydroxy, halogen, nitro, mercapto and the like.

By "substituted or unsubstituted aryl" is meant an aromatic ring structure containing from 6 to 14 aromatic ring carbon atoms. Preferably, the aryl group is unsubstituted phenyl. Where a substituent would be present, the aromatic ring could carry one or more of hydroxy, halogen, nitro, mercapto and the like.

By "substituted or unsubstituted arylalkyl" is meant a radical of the formula $-(CH_2)_n-Ar$ wherein n is 1 to 4 and Ar is an aromatic ring structure such as phenyl or naphthyl. Preferably, the arylalkyl group is unsubstituted benzyl. Where a substituent would be present, it could be attached to one of the methylene moieties or to the aromatic ring and could be selected from hydroxy, mercapto, halogen, nitro and the like.

By "substituted or unsubstituted heterocyclic group" is meant heterocyclic rings containing up to 8 ring atoms and containing 1 or 2 hetero atoms selected from nitrogen, oxygen and sulfur. As examples of this group, there may be mentioned pyridine, piperidine, morpholine, piperazine, thiazole, oxazole and the like.

Turning to R and $R_2$, each of these groups is independently selected from each of the possibilities as disclosed herein for $R_1$ plus substituted or unsubstituted acyl. Therefore, the definitions above for the various $R_1$ groups apply for R and $R_2$. In addition, by "substituted or unsubstituted acyl" is meant a group of the formula $$\overset{O}{\underset{\|}{-C}}-R_{10}$$

wherein $R_{10}$ is substituted or unsubstituted alkyl, alkenyl or aryl as hereinbefore defined. Preferably $R_{10}$ contains up to 4 carbon atoms and is unsubstituted.

At the present time, it is believed that only one of R, $R_1$ and $R_2$ should be a bulky substituent containing 5 or more atoms. Thus, preferred substituents are hydrogen, lower alkyl and lower acyl, the latter two being unsubstituted.

In addition to the above possibilities for R, $R_1$ and $R_2$, $R_1$ and R or R and $R_2$ can combine with each other to form a substituted or unsubstituted heterocyclic ring containing from 5 to 8 ring atoms. Thus, these heterocyclic rings will always contain 2 oxygen ring atoms. In addition, a third and at times, a fourth hetero atom could be present selected from oxygen, sulfur and nitrogen. Preferably, R and $R_1$ or R and $R_2$ combine to form a 5 or 6-membered ring which is unsubstituted or is substituted by lower alkyl, oxygen, sulfur, lower alkenyl and the like, wherein the lower alkyl or lower alkenyl group could carry further substitutions selected from hydroxy and halogen.

As used herein, "halogen" includes fluorine, chlorine, bromine and iodine, but preferably is fluorine or chlorine.

Where R and $R_1$ or R and $R_2$ combine to form a ring, it is preferred that the remaining $R_1$ or $R_2$ radical is not a bulky substituent, that is, contains no more than about 4 or 5 atoms.

The following formulae (IIA), (IIB) and (IIC) set forth preferred structures for —Z—.

(IIA)   (IIB)   (IIC)

In formula (IIA), each of $R_4$ and $R_5$ is independently selected from the group consisting of hydrogen, lower alkyl and lower acyl. By "lower" is meant up to about 4 to 5 carbon atoms. On the other hand, $R_3$ is hydrogen or lower alkyl. Of course, the provisos discussed with respect to formula (II) will apply with formula (IIA).

Turning to formulae (IIB) and (IIC), Q and $Q_1$ will complete a heterocyclic ring containing at least 5 atoms, up to 8 ring atoms. At times, an additional oxygen atom, nitrogen atom and/or sulfur atom as a hetero atom can be present. Q and $Q_1$ can be represented by (a)

$$\overset{\diagdown}{\underset{\diagup}{C}}=X$$

wherein X is sulfur or oxygen, (b)

$$\overset{\diagdown}{\underset{\diagup}{C}}\overset{R_8}{\underset{R_9}{\diagup}}$$

wherein preferably one of $R_8$ and $R_9$ is hydrogen, lower alkyl, lower alkenyl, aryl (ex phenyl), arylalkyl (ex benzyl), or alkanoyl or aroyl (ex acetyl or benzoyl), and the other is hydrogen, lower alkyl or lower alkenyl; or (c) $-(CH_2)_n$ wherein n is 2 to 10.

In certain instances substituents such as those disclosed hereinbefore are contemplated.

At the present time, one group of preferred compounds are those wherein Q and $Q_1$ are $$\overset{\diagdown}{\underset{\diagup}{C}}=O \quad \text{or} \quad \overset{\diagdown}{\underset{\diagup}{C}}\overset{\diagup\text{lower alkyl}}{\underset{\diagdown\text{lower alkyl}}{}}$$

Another group of preferred compounds at this time are those wherein Q and $Q_1$ are $$\overset{\diagdown}{\underset{\diagup}{C}}=O \quad \text{or} \quad \overset{\diagdown}{\underset{\diagup}{C}}\overset{\diagup\text{lower alkyl}}{\underset{\diagdown\text{lower alkyl}}{}}$$

and the remaining $R_1$ or $R_2$ is hydrogen or lower alkyl.

With the exception of the proviso concerning the epimers of methyl 20-dihydroprednisolonate discussed herein, all isomers and mixtures thereof are contemplated herein, including racemic mixtures. The racenates or other epimeric mixtures may be those occurring from synthesis procedures used to prepare the compounds of the invention or may be formed by admixing the separately obtained epimers. For reasons which are unknown at the present time, perhaps involving small amounts of impurities, an epimeric mixture resulting from synthesis will not necessarily have the same pharmacological activity as a mixture in the same proportion of the same epimers which were first separated or separately synthesized, purified, and then admixed in the same proportional ratio.

In general, the compounds of the present invention can be synthesized using the procedures disclosed in the prior art, particularly the Lewbart et al references mentioned hereinbefore. A convenient route for preparing many of the compounds of this invention is through the 21-dehydroprednisolone hemiacetal, particularly where one is interested in obtaining the 20α or 20β epimers.

The following examples illustrate preparation of some of the compounds of this invention, and are presented only for illustrative purposes.

EXAMPLE 1

Prednisolone to the glyoxal hemiacetal

To a solution of 11β,17α,21-trihydroxy-1,4-pregnadiene-3,20-dione (1.08 g) in methanol (75 ml) was added 150 mg. of copper (II) acetate in an equal volume of methanol. Oxygen was bubbled in for 30 minutes and after addition of ethylenediamine tetraacetic acid disodium salt (150 mg) in water (10 ml), the mixture was concentrated in vacuo. The fine, white precipitate was filtered off, washed with water and dried. Recrystallization from methanol afforded 1.08 g (93%) of 21-methoxy,11β,17α,21-trihydroxy-1,4-pregnadiene-3,20-dione, m.p. 173°–183°.

EXAMPLE 2

Methyl Dihydroprednisolonates from the glyoxal hemiacetal

To a solution of 21-methoxy-11β,17α,21-trihydroxy-1,4-pregnadiene-3,20-dione (3.90 g) in methanol (125 ml) was added water (1.0 l) and 1N sodium hydroxide (200 ml) under a nitrogen blanket. The solution was stirred at room temperature for 15 minutes, saturated with sodium chloride, and extracted with ethyl acetate. This small, neutral fraction was discarded. The aqueous layer was acidified with hydrochloric acid and re-extracted with ethyl acetate, affording the crude epimeric acids. A methanol solution of the acids was treated with excess ethereal diazomethane. Fractional crystallization of the product from methanol gave 1.79 g of methyl 11β,17α,20α-trihydroxy-3-oxo-1,4-pregnadien-21-oate mp 255°–257°. The mother liquor was subjected to preparative high performance liquid chromatography in aqueous methanol on an octadecyl silane column which provided baseline separation of the epimers. An additional 0.15 g of 20α epimer raised the yield to 1.94 g (49.7%). Crystallization of the less mobile, major fraction from ethyl acetate supplied 0.789 of methyl 11β,17α,20β-trihydroxy-3-oxo-1,4-pregnadien-21-oate (m.p. 176°–178°) in a yield of 20.0%.

EXAMPLE 3

Acetylation of methyl 11β,17α,20α-trihydroxy-3-oxo-1,4-pregnadien-21-oate

The 20α methyl ester (250 mg) was treated with 0.5 ml each of pyridine and acetic anhydride for one hour at room temperature. The reaction mixture was diluted with methylene chloride and washed successively with dilute HCl, dilute NaOH, and water. Crystallization of the product from acetone-isooctane afforded methyl 20α-acetoxy-11β,17α-dihydroxy-3-oxo-1,4-pregnadien-21-oate as hairy needles, m.p. 235°–236°.

EXAMPLE 4

Acetonation of methyl 11β,17α,20α-trihydroxy-3-oxo-1,4-pregnadien-21-oate

To 200 mg of the 20α methyl ester in methanol (10 ml) and acetone (190 ml) was added 0.5 ml of 70% perchloric acid. After 13 hours at room temperature there was added 1.0 g of sodium bicarbonate and the mixture was concentrated in vacuo nearly to dryness. The crude product was partitioned between methylene chloride and water and the oily residue obtained from the organic layer was subjected to preparative reverse phase HPLC, affording methyl 17α,20α-isopropylidinedioxy-11β-hydroxy-3-oxo-1,4-pregnadien-21-oate as prisms from acetone-isooctane, m.p. 199°–201°, in a yield of 162 mg (74%).

EXAMPLE 5

Phosgenation of methyl 11β,17α,20β-trihydroxy-3-oxo-1,4-pregnadien-21-oate

To a solution of the 20β methyl ester (200 mg) in pyridine (5 ml) at 0° C. while stirring magnetically there was added drop-wise a mixture of 12.5% phosgene in toluene (1.5 ml) and toluene (3.5 ml) over a five minute period. The mixture stood at 0° C. for ten minutes, then was washed with dilute HCl and water. Crystallization of the product from ethyl acetate furnished methyl 17α,20β-cyclocarbonyldioxy-11β-hydroxy-3-oxo-1,4-pregnadien-21-oate as equilateral prisms in a yield of 185 mg. (87%), m.p. 260°–261.5°.

EXAMPLE 6

Saponification of methyl 11β,17α,20α-trihydroxy-3-oxo-1,4-pregnadien-21-oate

A solution of the 20α methyl ester (1.0 g) in methanol (15 ml) was diluted with water (30 ml) and 1N NaOH (20 ml). The mixture was concentrated in a nitrogen stream, acidified with dilute HCl and the resulting white precipitate filtered off and washed with water. The filtrate was extracted with ethyl acetate. Recrystallization of the combined precipitate and ethyl acetate extract afforded 850 mg. (88%) of 11β,17α,20α-trihydroxy-3-oxo-1,4-pregnadien-21-oic acid as prisms from methanol, m.p. 219°–221°.

EXAMPLE 7

Acetonation of the 20α acid

To a solution of 11β,17α,20α-trihydroxy-3-oxo-1,4-pregnadien-21-oic acid (200 mg) in acetone (200 ml) was added 0.5 ml of 70% perchloric acid. After 20 minutes at room temperature there was added 600 mg. of sodium bicarbonate and the product was recovered by partitioning the residue between methylene chloride and water. Crystallization from acetone provided 20α,21- isopropylidinedioxy-11β,17α-dihydroxy-3-oxo-1,4-pregnadien-21-oate as prisms, m.p. 266°–269°, in a yield of 160 mg. (72%).

EXAMPLE 8

Cathylation of methyl 11β,17α,20β-trihydroxy-3-oxo-1,4-pregnadien-21-oate

A solution of the 20β methyl ester (200 mg) in cold pyridine (2 ml) was treated with 0.15 ml of ethyl chlorocarbonate. The reaction mixture stood overnight at room temperature. The product was recovered after dilution with ice water and methylene chloride and washing the organic layer with dilute HCl and water. Crystallization from methanol yielded methyl 20β-carboethoxy-11β,17α-dihydroxy-3-oxo-1,4-pregnadien-21-oate as leaflets, m.p. 233°–235°, in a yield of 200 mg (88%).

EXAMPLE 9

Preparation of t-butyl 11β,17α,20β-trihydroxy-3-oxo-1,4-pregnadien-21-oate

A solution of 11β,17α,20β-trihydroxy-3-oxo-1,4-pregnadien-21-oic acid (250 mg) in 25 ml of t-butyl acetate was treated with 0.25 ml of 70% perchloric acid. After stirring magnetically for two hours the reaction mixture was diluted well with methylene chloride and washed with excess dilute NaOH and water. The neutral fraction was subjected to column chromatography on silica gel in ethyl acetate-isooctane (1:1). After emergence of several unknown products the t-butyl ester was recovered and crystallized from methanol as long needles in a yield of 105 mg (36.6%), m.p. 184.5°–186.5°.

The pharmacologically active compounds of this invention may be administered alone or in combination with acceptable pharmaceutical carriers, the choice of which is determined by the selected route of administration, the solubility of the compound and standard pharmaceutical practice. In general, the dosage of the compounds of the present invention would be approximately of the same order of magnitude as the dosages of prednisolone. Indeed, certain of these compounds are useful to treat the types of medical conditions often treated with prednisolone. With this in mind, and based on experimentation carried out to date, the dosage range for compounds of the present invention would be about 0.05 to 0.5 mg/kg, 1 to 3 times per day. A total dosage for an average human adult would be expected to be in the range of about 2.5 to 25 mg/day, subdivided into three or four doses.

For oral administration, the compounds may be administered in the form of tablets, capsules and the like containing excipients such as starch or milk sugar. Aqueous suspensions and elixirs which may be sweetened or flavored may also be used. To apply these therapeutic agents topically, they may be prepared in the form of ointments, creams and salves, utilizing suitable bases, such as the hydrophilic cream type bases and hydrophobic ointment type bases routinely utilized with hydrocortisone topical preparations. The active ingredient would most likely be present in an amount of about 0.25 to 2.0% by weight of the ointment or cream. Aqueous and non-aqueous suspensions can be employed for the preparation of injectibles, such as those to be used in intra-articular, subcutaneous or intramuscular dosage forms. In these cases, various suspending and wetting agents, as is well known in the art, may be added to the compositions to obtain a suspension which does not tend to settle out easily or to pack down in a storage bottle. Again, standard pharmaceutical practice would be employed.

EXAMPLE 10

This example sets forth pharmacological activities of representative compounds of the present invention. Groups of 6 rats each were used for each compound.

Measurement of Anti-inflammatory Activity by the Cotton Pellet Granuloma Bioassay Adult Male Sprague-Dawley rats weighing 120–140 g were maintained on standard laboratory chow with water ad libitum and kept under controlled conditions for one week prior to their use. Inhibition of granuloma formation was determined by a modification of the method of Meier, Schuler and Desaulles, "Zur Frage des Mechanismus der Hemmung des Bindegewebswachstums durch Cortisone", Experimentia, 6, 469–471 (1950). Cotton pellets weighing 35±1 mg cut from dental rolls were impregnated with 0.2 or 0.4 ml of steroid solution in acetone and the solvent was removed by evaporation. The cotton pellets were subsequently injected with 0.2 ml aqueous solution of antibiotics (1 mg penicillin G sodium and 1.3 mg dihydrostreptomycin/ml). Two cotton pellets were implanted subcutaneously, one in each axilla of the rat under light ether anesthesia. Cotton pellets containing only the antibiotic solution were similarly implanted in control rats. Seven days later, the animals were sacrificed and the two pellets with their adhering granulomas were removed, dried for 48 hours in an oven at 60° C. and weighed. The increment in dry weight (difference between the initial and final pellets weight) is taken as a measure of granuloma formation. The adrenal, thymus and final body weights were also recorded. The adrenal and thymus weights were expressed as relative weights (mg tissue/100 g body weight).

Determination of Plasma Corticosterone Levels

The local and systemic effects of the steroid acid ester derivatives on pituitary adrenal axis were studied concomitantly with the cotton pellet granuloma bioassay. Blood samples were collected through cardiac puncture in heparinized tubes which were immediately centrifuged for 10 minutes. The plasma was removed and stored at −20° C. Plasma corticosterone levels were assayed by the modified fluorometric method of Vernikos-Danellis, Anderson, and Trigg, "Changes in Adrenal Corticosterone Concentration in Rats: Method of Bioassay for ACTH", Endocrinology, 79, 624–630 (1966).

The results of this experiment are set forth below.

All of the runs were not carried out at the same time; however, the degree of experimental reproducibility has been found to be high so that valid comparisons can be made between runs carried out at different times but using the same protocol. In each run, 0.25 mg of the test substance was impregnated into each cotton pellet.

| Test Substance | % Granuloma Inhibition | % Change Thymus Weight | % Change Adrenal Weight | % Change Plasma Corticosterone |
|---|---|---|---|---|
| 1 | 70.44 | −58.7 | −25.0 | −31.1 |
| 2 | 66.76 | −24.4 | −3.3 | −6.9 |
| 160A | 13.88 | −11.7 | +4.0 | +24.1 |
| 164A | 27.17 | −3.1 | +28.0 | +1.1 |

-continued

| | | | | |
|---|---|---|---|---|
| 165A | 24.40 | −20.2 | −3.9 | |
| 160C | 32.00 | −21.0 | −23.1 | |
| 185A | 3.28 | −4.1 | +2.0 | −32.8 |
| 184A | −6.03 | −10.9 | −6.8 | −36.5 |
| 173A | −20.49 | −6.6 | +12.9 | −49.2 |
| 177A | 11.06 | −28.8 | +7.1 | −35 |
| 171A | 63.73 | −10.8 | −7.5 | |
| 175A | 20.11 | −16.0 | +7.2 | +20.9 |
| 181A | 42.39 | −10.4 | +10.5 | −33 |
| 187A | −5.09 | −34.7 | +7.1 | −18 |

| | Compound |
|---|---|
| 1 | Prednisolone [11β,17,21-trihydroxy-1,4-pregnadiene-3,20-dione] |
| 2 | One of the Lee et al "P4" substances |
| 160A | Methyl 20 α-dihydroprednisolonate [Methyl 11β,17,20α-trihydroxy-3-oxo-1,4-pregnadien-21-oate] |
| 164A | Methyl 20β-dihydroprednisolonate |
| 165A | Methyl 20α-acetyldihydroprednisolonate [Methyl 20α-acetoxy-11β,17-dihydroxy-3-oxo-1,4-pregnadien-21-oate] |
| 160C | Methyl 20β-acetyldihydroprednisolonate |
| 185A | Methyl 20α-cathyldihydroprednisolonate [Methyl 20α-carboethoxy-11β,17-dihydroxy-3-oxo-1,4-pregnadien-21-oate] |
| 184A | Methyl 20β-cathyldihydroprednisolonate |
| 173A | Methyl 17,20α-cyclocarbonyldihydroprednisolonate [Methyl 17,20α-cyclocarbonyldioxy-11β-hydroxy-3-oxo-1,4-pregnadien-21-oate] |
| 177A | Methyl 17,20β-cyclocarbonyldihydroprednisolonate |
| 171A | Methyl 17,20α-acetonidodihydroprednisolonate [Methyl 17,20α-isopropylidenedioxy-11β-hydroxy-3-oxo-1,4-pregnadien-21-oate] |
| 175A | Methyl 17,20β-acetonidodihydroprednisolonate |
| 181A | 20α,21-acetonidodihydroprednisolonate [20α,21-isopropylidenedioxy-11β,17-dihydroxy-3-oxo-1,4-pregnadiene-21-oate] |
| 187A | 20β,21-acetonidodihydroprednisolonate |

I claim:

1. A compound of the formula (I)

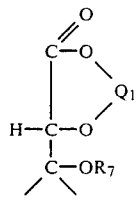 (I)

wherein Z is selected from the group consisting of:

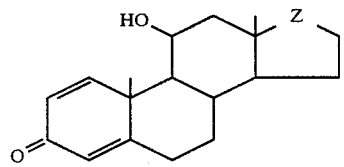 (IIB)

wherein $R_6$ is selected from the group consisting of hydrogen and lower alkyl, $R_7$ is selected from the group consisting of hydrogen, lower alkyl and lower acyl; wherein Q and $Q_1$ are selected from the group consisting of:

wherein X is O or S,

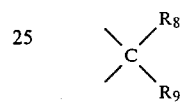

and $-(CH_2)_n-$
wherein each of $R_8$ and $R_9$ is independently selected from the group consistency of hydrogen, lower alkyl, aryl, arylalkyl, alkanoyl and aryl and n is an integer from 2 to 10.

2. A compound of claim 1 wherein $R_7$ is hydrogen.

3. A compound of claim 1 wherein Q and $Q_1$ are

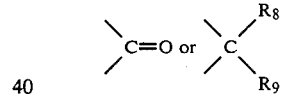

wherein $R_8$ and $R_9$ are lower alkyl.

4. A process for treating a patient in need of at least one of an anti-inflammatory medicine or a medicine to suppress the pituitary adrenal axis, which comprises administering to said patient an effective amount of a compound of any of claims 2 and 3.

5. The process of claim 4 comprising local administration.

6. The process of claim 4 comprising systemic administration.

7. The compound of claim 1, Methyl 17,20α-cyclocarbonyldihydroprednisolonate[Methyl 17,20α-cyclocarbonyldioxy-11β-hydroxy-3-oxo-1,4-pregnadien-21-oate].

8. The compound of claim 1, Methyl 17,20β-cyclocarbonyldihydroprednisolonate.

9. The compound of claim 1, Methyl 17,20α-acetonidodihydroprednisolonate[Methyl 17,20α-isopropylidenedioxy-11β-hydroxy-3-oxo-1,4-pregnadien-21-oate].

10. The compound of claim 1, Methyl 17,20β-acetonidodihydroprednisolonate.

11. The compound of claim 1, 20α,21-acetonidodihydroprednisolonate[20α,21-isopropylidenedioxy-11β,17-dihydroxy-3-oxo-1,4-pregnadiene-21-oate].

12. The compound of claim 1, 20β,21-acetonidodihydroprednisolonate.

* * * * *